Figure 1:
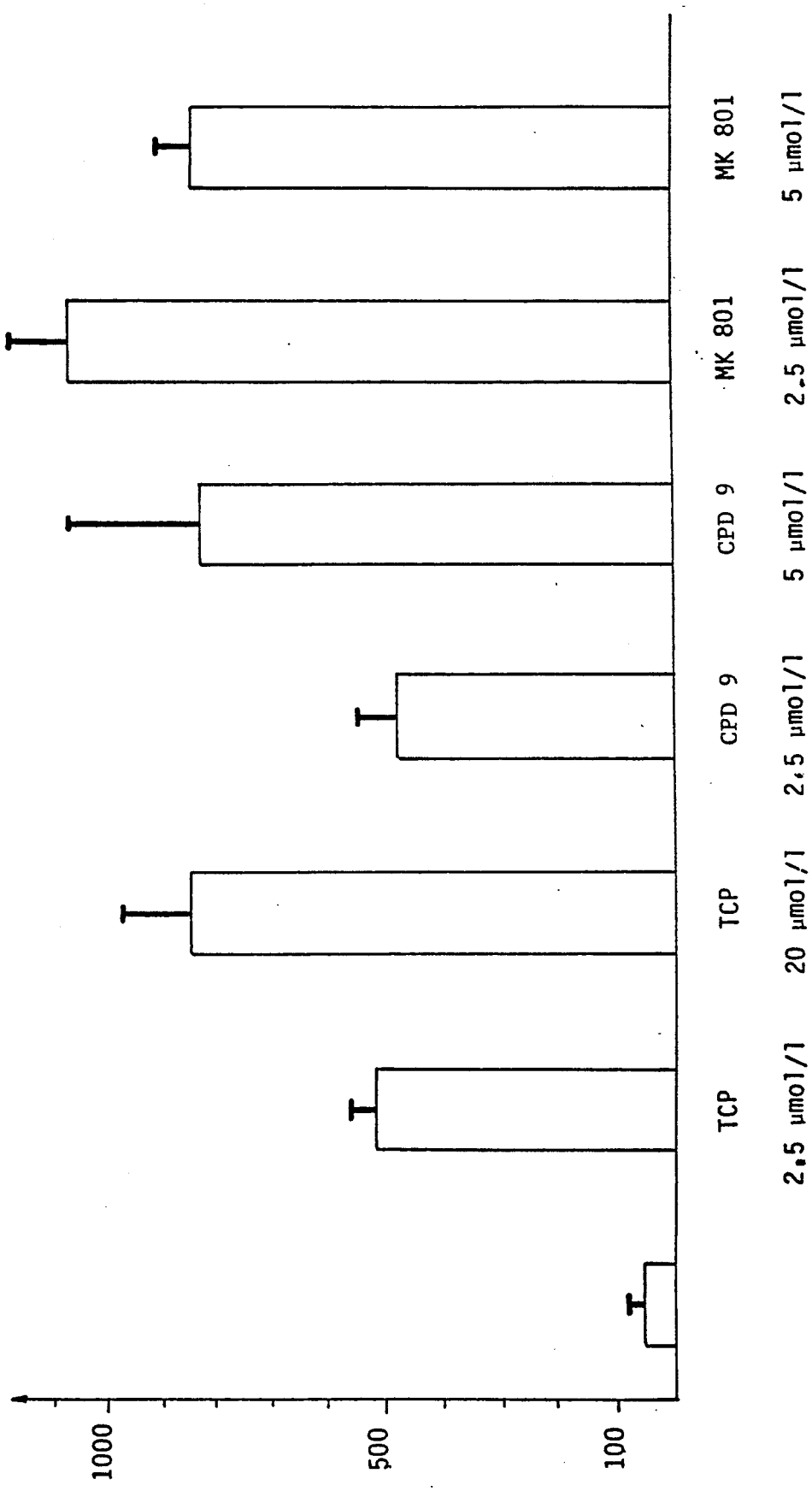

United States Patent [19]

Kamenka et al.

[11] Patent Number: 5,179,109
[45] Date of Patent: Jan. 12, 1993

[54] PHARMACEUTICAL COMPOSITIONS FOR NEUROPROTECTION CONTAINING ARYLCYCLOHEXYLAMINES

[75] Inventors: Jean-Marc Kamenka, Montpellier; Alain Privat, Clement-La-Riviere; Robert Chicheportiche; Gérard Rondouin, both of Montpellier, all of France

[73] Assignee: Centre National E La Recherche Scientifique, Paris, France

[21] Appl. No.: 499,491
[22] PCT Filed: Nov. 20, 1989
[86] PCT No.: PCT/FR89/00596
    § 371 Date: Jun. 21, 1990
    § 102(e) Date: Jun. 21, 1990
[87] PCT Pub. No.: WO90/05524
    PCT Pub. Date: May 31, 1990

[30] Foreign Application Priority Data

Nov. 21, 1988 [FR] France ............................ 8815106

[51] Int. Cl.$^5$ ................ A61K 31/445; A61K 31/435; A61K 31/44
[52] U.S. Cl. ................ 514/326; 514/277; 514/317; 514/336
[58] Field of Search ............ 514/315, 277, 317, 326, 514/336

[56] References Cited

FOREIGN PATENT DOCUMENTS 838748 6/1960 United Kingdom .

OTHER PUBLICATIONS

Chemical Abstracts, vol. 109, 1988, p. 19, No. 85738p.
Chemical Abstracts, vol. 89, 1978, p. 29, No. 190857t.
Neurol. Neurobiol., vol. 46, 1988, Alan R. Liss, Inc. J. W. McDonald et al., Comparison of Neuroprotective Effects of Competitive and Non-Competitive MNDA Antagonists Against NMDA Mediated Neurotoxicity in an in Vivo Perinatal Rat Model, pp. 601-604.
Neurosci. Lett., vol. 91, No. 2, Aug., 1988, Elsevier Scientific Pub. Ireland Ltd., G. Rondouin et al.: "Non-Competitive Antagonists of N-Methyl-D-Aspartate Receptors Protect Cortical and Hippocampal Cell Cultures Against Glutamate Neurotoxicity", pp. 199-203.
Brain Research, vol. 490, Jun. 19, 1989, Elsevier Science Pub. B. V. (Biomedical Div.), M. D. Tricklebank et al.: The Behavioural Effects of MK-801: A Comparison With Antagonists Acting Non-Competitively and Competitively at the NMDA Receptor, pp. 127-135.
Faseb, J., vol. 1, No. 6, 1987, Faseb, M. B. Robinson et al.: Glutamate and Related Acidic Excitatory Neurotransmitters: From Basic Science to Clinical Application, pp. 446-455.
Brain Research, vol. 152, 1978, J. P. Vincent et al.: Interaction of Phencyclidines with the Muscarinic and Opiate Receptors in the Central Nervous System, pp. 176-182.
European Journal of Pharmacology, vol. 167, Aug. 11, 1989, Elsevier Science Publishers B. V. (Biomedical Division), M. D. Tricklebank et al.: "The Behavioural Effects of MK-801: A Comparison with Antagonists Acting Non-Competitively and Competitively at the NMDA Receptor", pp. 127-135.
Olney, John et al., Eur. J. Pharmacology 141(1987) 357-361.

Primary Examiner—Frederick E. Waddell
Assistant Examiner—Diane Gardner
Attorney, Agent, or Firm—Pearne, Gordon, McCoy & Granger

[57] ABSTRACT

The invention relates to pharmaceutical compositions for neuroprotection containing arylcyclohexylamines. These compositions comprise an arylcyclohexylamine in accordance with the formulas:

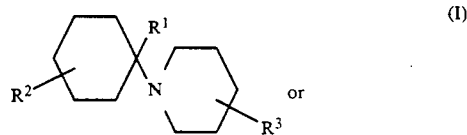

(I)

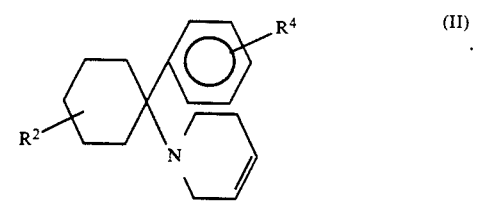

(II)

in which:
$R^1$ represents

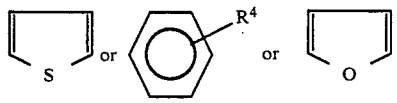

with $R^4$ being a hydrogen atom, a fluorine atom, an iodine atom or a methyl radical, $R^2$ stands for a hydrogen atom, the radical OH or the radical $CH_3$ and $R^3$ stands for hydrogen atom or the radical $CH_2R^5$ with $R^5$ representing H, OH, Cl, Br or $CH_3COO$, provided that $R^2$ and $R^3$ are not both a hydrogen atom, or an addition salt to a pharmaceutically acceptable acid of said arylcyclohexylamine.

10 Claims, 3 Drawing Sheets

PHARMACEUTICAL COMPOSITIONS FOR NEUROPROTECTION CONTAINING ARYLCYCLOHEXYLAMINES

The present invention relates to pharmaceutical compositions for neuroprotection containing arylcyclohexylamines.

More specifically, it relates to the use of arylcyclohexylamines having a structure close to that of phencyclidine (PCP), i.e. 1-(1-phenylcyclohexyl)-piperidine of formula:

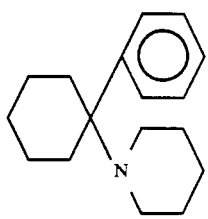

or that of ((2-thienyl)-1 cyclohexyl)-N-piperidine (TCP) of formula:

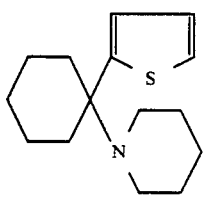

Phencyclidine (PCP), whose pharmacological activity was studied in about 1958, was introduced as an analgesic and anesthetic under the name SERNYL and was then abandoned due to its secondary psychodysleptic effects.

Like PCP, TCP belongs to the series of arylcyclohexylamines and can be used in anesthesia as an additive or for the treatment of hyper-excitability due to its depressive effect and as is described in U.S. Pat. No. 2,921,076 of Parke, Davis & Co.

Thus, arylcyclohexylamines have never been used in neuroprotection. However, recent studies on PCP revealed that this molecule could act as a non-competitive antagonist of N-methyl-D-aspartate (NMDA), which is an interesting property for cerebral protection, particularly against the damage associated with the presence of glutamate.

Thus, the toxicity of exciting or excitatory amino acids such as glutamates is the main cause of damage to the brain encountered during ischemia, anoxia, hypoglycemia or epilepsy. It is also assumed that the toxicity of amino acids is involved in certain neurodegenerative disorders.

The molecules which act as NMDA antagonists can be used in neuroprotection. However, in the case of PCP, the secondary psychodysleptic effects prevent such a use.

In addition, research has been carried out to find other molecules acting as an NMDA antagonist and without suffering from said disadvantage.

The present invention is specifically directed to novel pharmaceutical compositions for neuroprotection and which contain arylcyclohexylamines having a non-competitive antagonizing effect with respect to NMDA receptors, but not having the disturbing secondary or side effects of PCP.

According to the invention, the pharmaceutical composition for neuroprotection comprises an arylcyclohexylamine in accordance with the formulas:

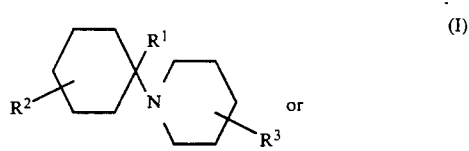

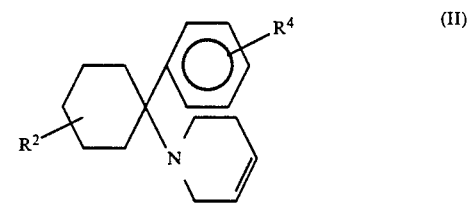

in which:
$R^1$ represents

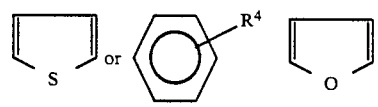

with $R^4$ being a hydrogen atom, a fluorine atom, an iodine atom or a methyl radical, $R^2$ represents a hydrogen atom, the radical OH or the radical $CH_3$ and $R^3$ represents a hydrogen atom or the radical $CH_2R^5$ with $R^5$ representing H, OH, Cl, Br or $CH_3COO$, provided that $R^2$ and $R^3$ are not both a hydrogen atom, or an addition salt to a pharmaceutically acceptable acid of said arylcyclohexylamine.

In this formula, when $R^1$ represents the thienyl or furanyl radical, the latter can be connected to the cyclohexyl nucleus by a carbon in the ortho or meta position with respect to the heteroatom O or S of the furanyl or thienyl radical.

The arylcyclohexylamines used in the invention have a structure close to that of PCP or TCP, but differ therefrom by the presence of substituents giving them the properties of more selectively fixing to the site of the phencyclidine, while being non-competitive antagonists of NMDA, which are not fixed to the site of the NMDA and while having less affinity for the muscarinic receptors and opiate receptors than PCP, i.e. greatly reduced psychodysleptic properties.

Thus, these arylcyclohexylamines are non-competitive antagonists of the NMDA receptor of exciting amino acids. Thus, they are fixed to the receptor of the PCP and selectively block the entry of the $Ca^{2+}$ and $Na^+$ ions passing through the ionic channel activated by the agonists of the NMDA receptor. This property forms the basis for the neuroprotective properties which can be used for combating aging and acute cerebral attacks. Thus, the arylcyclohexylamines according to the invention can be used in cases of ischemia and cerebral traumatism and also for protection against aging.

In cerebral attacks, there is a large production of glutamate, which leads to necrosis of the cells. This release is particularly important when the blood circulation is reestablished, which produces a progression of the necrosis of the neurons. However, in the presence of the arylcyclohexylamines according to the invention and which act as non-competitive antagonists of the NMDA receptors, there is a blocking of the toxic effects of the glutamate.

Certain TCP derivatives usable in the invention were described by Vincent et al in Brain Research, 152, 1978, pp. 176–182. However, this article only studied the affinity of the derivatives for muscarinic and opiate receptors in order to determine their psychodysleptic properties, whereas the invention is more particularly based on the non-competitive antagonizing effect of the compounds with respect to NMDA receptors. Thus, it could not be deduced from the said document that the compounds according to the invention would be usable for neuroprotection.

Patent GB-A-838 748 (Parke, Davis & Co.) describes heterocyclic compounds, which can also include certain TCP derivatives usable in the invention. However, in this case, it is a question of use as an additive for anesthesia and not as medicaments having a neuroprotective effect.

Thus, the invention relates to the use of arylcyclohexylamines in accordance with the aforementioned formulas (I) and (II), for the production of neuroprotective medicaments for preventing cerebral attacks which can occur during acute ailments such as ischemia, anoxia, hypoglycemia or epilepsy, or for protecting the brain against aging.

The invention also relates to the use of TCP of formula:

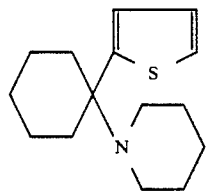

for the production of a neuroprotective medicament for protecting the brain against aging.

According to a first embodiment of the invention, the arylcyclohexylamine is in accordance with formula (I) and has a structure close to that of PCP. In this case, $R^1$ represents a radical of formula:

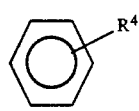

in which $R^4$ stands for a hydrogen atom, a fluorine atom or a methyl radical.

Examples of such arylcyclohexylamines are:
arylcyclohexylamines of formula (III):

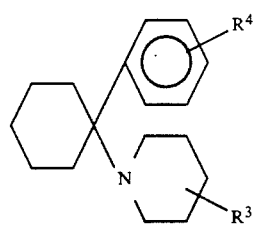

in which $R^3$ stands for the methyl radical or the radical $CH_2R^5$ with $R^5$ representing OH or $CH_3COO$ and $R^4$ represents a hydrogen atom;

arylcyclohexylamines of formula (IV):

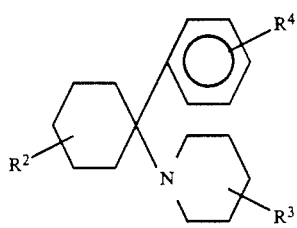

in which $R^2$ is the methyl radical, $R^3$ the radical $CH_2R^5$ with $R^5$ representing OH and $R^4$ is a fluorine atom; and
arylcyclohexylamines of formula:

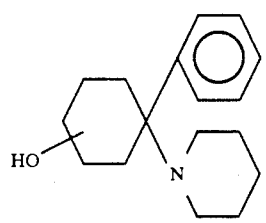

According to a second embodiment of the invention, the arylcyclohexylamine is in accordance with formula (I) and has a structure close to that of TCP. In this case, $R^1$ represents the thienyl radical, which can be connected to the cyclohexyl nucleus by means of a carbon in the ortho or meta position with respect to the S atom of the thienyl radical.

Examples of such arylcyclohexylamines are:
arylcyclohexylamines of formula (VI):

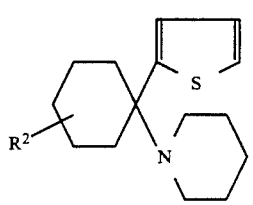

in which $R^2$ is the methyl radical:
arylcyclohexylamines of formula (VII):

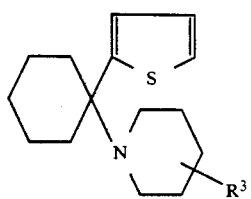
(VII)

in which R³ is the radical CH₂R⁵ with R⁵ representing OH or Cl;

and arylcyclohexylamines of formula (VIII):

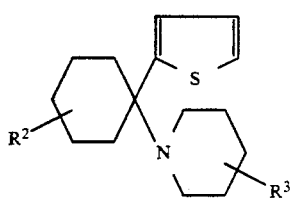
(VIII)

in which R² is the methyl radical and R³ the CH₂OH radical.

In the arylcyclohexylamines according to the invention, the position of the substituents R², R³ and R⁴ has an effect on the properties obtained.

Preferably when R² is the radical CH₃, it is in the ortho position. When R² is the radical OH, it is preferably also in the ortho position. When R³ is the substituent CH₂R⁵, its position with respect to the nitrogen atom also has an effect on the result obtained and it is generally in the meta or para position, preferably in the meta position. When R¹ is a substituted phenyl radical, the substituent R⁴ is preferably in the meta position.

The arylcyclohexylamines used in the invention can be in the form of different stereoisomers and all stereoisomers are suitable for the purposes of the invention. However, when R² is not a hydrogen atom and is in the ortho or meta position, preference is given to the cis-piperidine isomers, which are the most effective. When R² is not a hydrogen atom and is in the para position, preference is given to the use of trans-piperidine isomers.

Thus, preference is given to the use of the amino arylcyclohexyl of formula:

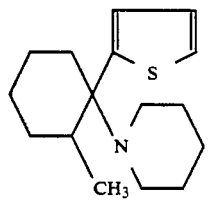
(IX)

with CH₃ in the cis position with respect to the piperidine.

Certain arylcyclohexylamines according to the invention can also exist in the form of optical isomers and according to the invention it is possible to use either optical isomers alone, or the racemic mixture.

The invention also relates to a process for preventing cerebral attacks in man or animals, which consists of administering to man or the animal a therapeutically effective quantity of an arylcyclohexylamine according to the aforementioned formulas (I) or (II) or TCP in controlling cerebral aging.

The arylcyclohexylamines according to the invention can be prepared by conventional processes, e.g. from the following compounds:

piperidines of formula:

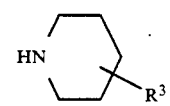
(X)

in which which R³ has the meaning given hereinbefore, tetrahydropyridine of formula:

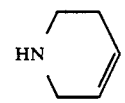
(XI)

cyclohexanones of formula:

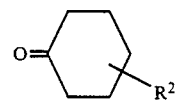
(XII)

in which R² has the meaning given hereinbefore,
benzene halides of formula:

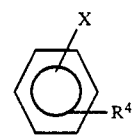
(XIII)

in which X represents an iodine, bromine or chlorine atom and R⁴ has the meaning given hereinbefore and
thiophene halides of formula:

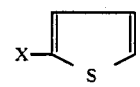
(XIV)

in which X has the meaning given hereinbefore.

Several synthesis processes can be envisaged and their choice is in particular dependent on the position of the substituent R² and the isomer which it is wished to obtain. Three synthesis processes which can be used are described hereinafter.

SYNTHESIS PROCESS I

This synthesis process takes place in the following two stages:

a) the preparation of alpha-aminonitriles from piperidines of formula (X) or pyridines of formula (XI) and cyclohexanones of formula (XII) and then b) the reaction of the alpha-aminonitriles with the benzene halides of formula (XIII) or thiophene halides of formula (XIV).

Alpha-aminonitrile complies with the formula:

(XV) (XVI)

in which R² and R³ have the meanings given hereinbefore.

It is prepared by a variant of the Strecker reaction, which takes place in the anhydrous organic medium.

For this purposes, cyanohydrin in acetone (cyanide ion donor) is reacted with 1) the piperidine of formula (X) or the pyridine of formula (XI) and 2) a cyclohexanone of formula (XIII), in the presence of magnesium sulphate which acts as a dehydrating agent and in a solvent of the dimethylacetamide (DMA) type. After treatment and purification, the corresponding alpha-aminonitrile is isolated with a purity of at least 95% and is used as such in the remainder of the synthesis.

In the second stage, said alpha-aminonitrile is reacted with a benzene halide of formula (XIII) or a thiophene halide of formula (XIV) using the Bruylants synthesis. This synthesis consists of reacting the alpha-aminonitrile with a Grignard reagent obtained from benzene or thiophene halide of formulas (XIII) or (XIV) in ether or anhydrous tetrahydrofuran (THF). After an appropriate treatment and purification, the sought arylcyclohexylamine is isolated. Anhydrous hydrochloric gas is then bubbled into an ethereal solution of pure arylcyclohexylamine and in this way the corresponding hydrosoluble hydrochloride is precipitated.

This synthesis process is stereospecific and consequently only gives access to one of the possible isomers. Thus, when the substituent R² is in the ortho or para position, the cis-piperidine isomer is obtained, whereas when R² is in the meta position the trans-isomer is obtained.

SYNTHESIS PROCESS II

This synthesis takes place in the following four stages:

a) preparation of benzyl alcohol of formula:

(XVII)

A cyclohexanone of formula (XII) is reacted with a Grignard reagent obtained from benzene or thiophene halides of formulas (XIII) or (XIV) in anhydrous ether. This gives benzylalcohols, which then undergo rapid purification.

b) preparation of the corresponding azide derivatives of formula:

(XVIII)

According to a procedure close to that used in the Schmidt and Curtius reactions, the alcohol function is substituted by the azide function by adding the preceding crude alcohols to a sodium azide suspension in trichloroacetic acid and cold chloroform. After treatment, a crude mixture of epimeric azide is isolated and then used as such.

c) reduction of the azides:

The preceding mixture is reacted with Raney nickel in isopropanol to supply, after treatment, a mixture of epimeric primary amines used as such.

d) formation of the piperidine cycle and purification:

1,5-dibromopentane is reacted hot in acetonitrile on the preceding mixture of primary amines. Following treatment, isolation takes place of a residue essentially containing a crude mixture of two stereoisomers. It is possible to separate the two pure isomers by chromatography and in this way obtain the sought compound. By anhydrous hydrochloric gas bubbling into the ethereal solution of the separated derivative, the corresponding hydrosoluble hydrochloride is precipitated.

Thus, process (II) gives access to two possible isomers and in particular that not obtained by process (I). However, process (II) cannot be used for the preparation of derivatives of formula (II) or for the preparation of derivatives of formula (I) having a substituent R³.

SYNTHESIS PROCESS III

This synthesis process comprises the following stages:

a) formation of benzylalcohol of formula (XVII) as in synthesis process (II) by reacting a cyclohexanone of formula (XII) in which R² is a hydrogen atom with the Grignard reagent obtained from the benzene or thiophene halide of formulas (XIII) or (XIV). This is followed by rapid purification of the alcohol and its use as such in the remainder of the synthesis.

b) Formation of arylcyclohexene of formula:

(XIX)

The previously obtained alcohol is dehydrated in the acid medium to supply the sought arylcyclohexene.

c) Formation of the corresponding epoxides:

The corresponding epoxide of formula:

(XX)

is formed by using an appropriate peracid.

d) Opening of the epoxides by piperidine:

The previously obtained epoxide is opened hot by piperidine in a methanol medium to give a majority benzylalcohol and a minority 2-hydroxyarylcyclohexylamine of formula:

(XXI)

constituting the sought product.

By bubbling anhydrous hydrochloric gas into the ethereal solution of the product obtained, the corresponding hydrosoluble hydrochloride is precipitated.

Process III is also stereospecific and leads to the isomer with the OH trans-piperidine. Moreover it only makes it possible to easily obtain the hydroxylated compounds in the 2-position, which cannot be prepared by the two other processes.

In order to prepare the medicament according to the invention, it is possible to use arylcyclohexylamines of formulas (I) or (II), or their addition salts by combination with pharmaceutically acceptable acids. The usable acids are e.g. hydrochloric, sulphuric and tartaric acid.

Generally, arylcyclohexylamine or one of its addition salts of the pharmaceutically acceptable acids is mixed with an appropriate pharmaceutically acceptable, solid or liquid vehicle or support and optionally with other pharmaceutically acceptable additives.

Thus, for the preparation of the medicaments, an addition salt can be dissolved in the acids of arylcyclohexylamine in an aqueous solution orally injectable or administrable, e.g. physiological serum.

It is also possible to include the arylcyclohexylamines according to the invention in solid preparations to e.g. obtain orally administrable tablets, or slow release medicaments in implant form and using conventional procedures.

The generally administered doses are between 0.1 and 5 mg/kg. When the pharmaceutical composition is in the form of a solution, the arylcyclohexylamine solution concentration is such that the administered volume varies between 0.5 and 2 ml.

When the medicament according to the invention is used for the treatment of acute cerebral ailments, e.g. in the case of ischemia, hypoglycemia or epilepsy, preference is generally given to the administration of a single relatively high dose, e.g. by intravenous injection, in order to obtain the maximum effect.

When the medicament is used for protection against aging, the doses are generally lower and can be administered at a rate of one or two monthly. For this use, preference is given to administration methods using tablets or implants.

Other features and advantages of the invention can be better gathered from the following illustrative, non-limitative examples and with reference to the attached drawings, wherein show:

FIG. 1 A graph showing the survival rate of neurons in an in vitro culture treated by different compounds.

FIGS. 2 to 5 Micrographs of treated and untreated mouse brain sections.

EXAMPLE 1

Preparation of cyano-1((methyl-4piperidino)-1)-1 cyclohexane (synthon I).

Mixing takes place of 9.8 g (0.1M) of cyclohexanone, 13.4 g (0.15M) of cyanohydrin acetone, 63 g (0.5M) of $MgSO_4$ (dried) in 14.9 g (0.15M) of 4-methyl piperidine and 8.7 g (0.1M) of DMA (dimethylacetamide). Strong stirring takes place at 45° C. for 48 h and it is then poured into a large volume of water and ice violently stirred for 30 min. After ether extraction, drying ($Na_2CO_3$) and vacuum evaporation of the solvent, a solid residue is obtained which, after crystallization in hexane or petroleum ether, gives 15.5 g (75%) of synthon I in the form of a whitish solid with a purity equal to or greater than 95%, which is adequate for the remaining syntheses, which is identified by infrared spectrometry.

EXAMPLE 2

Preparation of the cyano-1 ((tetrahydro-1,2,5,6pyridino)-1)-1 cyclohexane (synthon II).

15.1 g (0.15M) of cyclohexanone, 13.9 g (0.16M) of cyanohydrin acetone, 92 g (0.77M) of $MgSO_4$ (dried) are mixed in 22 g (0.3M) of 1,2,5,6-tetrahydropyridine and 26.1 g (0.3M) of DMA. Strong stirring takes place at 45° C. for 48 h and it is then poured into a large volume of water and ice violently stirred for 30 min. After extraction with ether, drying ($Na_2CO_3$) and vacuum evaporation of the solvent, a brownish yellow solid residue is obtained which, after crystallization in hexane or petroleum ether, gives 20 g (70%) of synthon II in the form of a yellowish solid with a purity at least equal to 95%, which is adequate for the remainder of the syntheses and which is identified by infrared spectrometry and mass spectrometry coupled with gas chromatography ((GC/MS). For GC/MS use is made of a 25 m OVI capillary column. The conditions and results obtained are as follows: injector temperature 100° to 250° C. (20° C./min), oven temperature: 200° C., retention time: 4.84 min, m/e 190.2.

EXAMPLE 3

Preparation of the cyano-1 (hydroxymethyl-3piperidino)-1 cyclohexane (synthon III).

20 g (0.2M) of cyclohexanone, 26 g (0.3M) of cyanohydrin acetone and 49 g (0.4M) of $MgSO_4$ (dried) are mixed in 30.3 g (0.3M) of 3-hydroxymethyl piperidine and 17.8 g (0.2M) of DMA. Strong stirring takes place at 45° C. for 48 h and then it is poured into a large volume of water and ice violently stirred for 30 min. This gives a white precipitate, which is suction filtered and dried in vacuo. In this way 23.1 g (85%) of aminonitrile (synthon III) are isolated of purity $\geq 95\%$, which is adequate for the remaining syntheses and which is identified by infrared spectrometry and mass spectrometry coupled with gas chromatography (GC/MS). A 25 m OV1 capillary column is used for the GC/MS. The conditions and results obtained are as follows: injector temperature 50° to 230° C. (10° C./min), oven temperature: 250° C., retention time: 13.92 min, m/e 222.1.

EXAMPLE 4

Preparation of the cyano-1 r-(hydroxymethyl-3piperidino)-1)-1-t-methyl-4-cyclohexane (synthon IV).

15 g (0.13M) of 4-methyl cyclohexanone, 11.3 g (0.13M) of cyanohydrin acetone and 80.4 g (0.67M) of $MgSO_4$ (dried) are mixed in 30.8 g (0.27M) of 3-hydroxymethyl-piperidine and 11.3 g (0.13M) of DMA. Strong stirring takes place at 45° C. for 48 h and it is then poured into a large volume of water and ice violently stirred for 30 min. After extraction with ether, drying ($Na_2CO_3$) and vacuum evaporation of the solvent, a whitish solid residue is obtained which, after crystallization in hexane or petroleum ether, gives 22.2 g (70%) of a white solid of purity $\geq 95\%$, which is adequate for the remainder of the syntheses. This compound contains the synthon IV and a small amount of a second possible stereoisomer, which does not constitute a disadvantage thereafter because, in the presence of a Grignard reagent (Lewis acid) it epimerizes into the majority isomer, which is the only one to react.

EXAMPLE 5

Preparation of the ((methyl-4 piperidino)-1)-1 phenyl-1 cyclohexane of formula

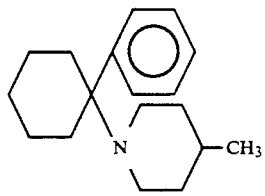

(compound no. 1)

The Grignard reagent resulting from the action of 8 g (0.05M) of bromobenzene on 2 g (0.08M) of magnesium in the form of turnings is prepared in 50 ml of anhydrous ether. To it is slowly added 5 g (0.02M) of synthon I dissolved in 50 ml of anhydrous ether. Stirring takes place for 12 h in the reflux condenser and the complex is decomposed by a cold saturated NH$_4$Cl solution and then, after settling, the liquids are extracted with ether (3×50 ml). The combined ethereal phases are extracted by an aqueous 20% HCl solution (2×50 ml). The acid liquids are neutralized by NH$_4$OH, extracted with ether (3×50 ml) and, after drying (Na$_2$SO$_4$), the combined ethers are evaporated in vacuo to give 5.8 g of a yellowish solid residue. The latter undergoes chromatography on alumina in pure petroleum ether in order to give 4.8 g (77%) of compound no. 1 in the form of an analytically pure, white solid melting at 53° to 54° C. By bubbling gaseous HCl into the ethereal solution of compound no. 1, its solid white hydrochloride is precipitated and, after recovery by suction filtering and vacuum drying, melts at 211° to 212° C.

Percentage analysis of the product of empirical formula C$_{18}$H$_{28}$NCl:

|   | Found | Calculated |
|---|-------|------------|
| C | 73.25 | 73.60 |
| H | 9.78  | 9.54  |
| N | 4.96  | 4.77  |

EXAMPLE 6

Preparation of the ((tetrahydro-1,2,5,6pyridino)-1)-1 (thienyl-2)-1 cyclohexane of formula:

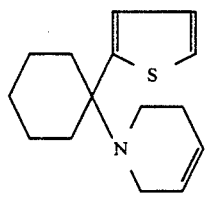

(compound no. 2)

The Grignard reagent resulting from the action of 8.15 g (0.05M) of 2-bromothiophene on 2 g (0.08M) of magnesium in the form of turnings is prepared in 50 ml of anhydrous ether. To it is slowly added 2 g (0.01M) of synthon II dissolved in 50 ml of anhydrous ether. Stirring takes place for 12 h in the reflux condenser, the complex is decomposed by a cold, saturated NH$_4$Cl solution and then, after settling, the liquids are extracted with ether (3×50 ml). The combined ethereal phases are extracted by an aqueous 20% HCl solution (2×50 ml). The acid liquids are neutralized by NH$_4$OH, extracted with ether (3×50 ml) and then the collected ethers, following drying (Na$_2$SO$_4$) undergo vacuum evaporation to give 2 g of a yellowish brown solid residue. The latter undergoes chromatography on silica in pure petroleum ether to give 1.3 g (53%) of compound no. 2 in the form of an analytically pure, white solid melting at 46° to 48° C. By bubbling gaseous HCl into the ethereal solution of this compound, its solid white hydrochloride is precipitated and, following recovery by suction filtering and vacuum drying, it melts at 163° to 164° C.

Percentage analysis of the product of empirical formula C$_{15}$H$_{22}$NSCl:

|   | Found | Calculated |
|---|-------|------------|
| C | 63.62 | 63.49 |
| H | 7.97  | 7.76  |
| N | 4.68  | 4.94  |

EXAMPLE 7

Preparation of the [(hydroxymethyl-3piperidino)-1]-1 (thienyl-2)-1 cyclohexane of formula:

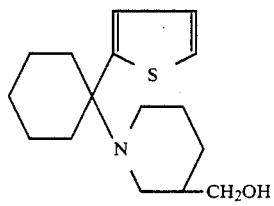

(compound no. 3)

The Grignard reagent resulting from the action of 57.6 g (0.35M) of 2-bromothiophene on 9 g (0.38M) of magnesium in the form of turnings is prepared in 350 ml of anhydrous ether. To it is slowly added 15.7 g (0.07M) of synthon III dissolved in 350 ml of anhydrous ether. Stirring takes place for 12 h in the reflux condenser, the complex is decomposed by a cold, saturated NH$_4$Cl solution and then, after settling, extraction takes place with ether (3×250 ml). The combined ethereal phases are extracted by an aqueous 20% HCl solution (2×200 ml). The acid liquids are neutralized by NH$_4$OH and extracted with ether (3×250 ml), whilst after drying (Na$_2$SO$_4$), the combined ethers are evaporated in vacuo to give 16.3 g of a yellowish oily residue. The latter is chromatographed on a high performance preparative chromatograph (two operations) on silica, in petroleum ether containing ether (80/20 v/v) to give 14.5 g (74%) of compound no. 3 in the form of an analytically pure, clear oil. By bubbling gaseous HCl into the ethereal solution of said compound, its solid white hydrochloride is precipitated and, after recovery by suction filtering and vacuum drying, melts at 170° to 171° C. (analytically pure).

Percentage analysis of the product of empirical formula C$_{16}$H$_{26}$NOSCl:

| | Found | Calculated |
|---|---|---|
| C | 60.59 | 60.86 |
| H | 8.11 | 8.24 |
| N | 4.16 | 4.44 |

EXAMPLE 8

Preparation of the [(hydroxymethyl-3piperidino)-1]-1phenyl-1 cyclohexane of formula:

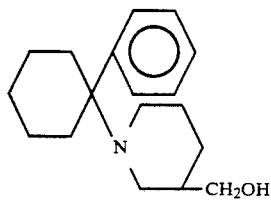

(compound no. 4)

The Grignard reagent resulting from the action of 55.5 g (0.35M) of bromobenzene on 9 g (0.38M) of magnesium in the form of turnings is prepared in 350 ml of anhydrous ether. To it is slowly added 15.7 g (0.07M) of synthon III dissolved in 350 ml of anhydrous ether. Stirring takes place for 12 h in the reflux condenser, the complex is decomposed by a cold, saturated NH4Cl solution and then, after settling, ether extraction takes place (3×250 ml). The combined ethereal phases are extracted by an aqueous 20% HCl solution (2×200 ml). The acid liquids are neutralized by NH4OH, extracted with ether (3×250 ml) and the collected ethers, after drying (Na2SO4) undergo vacuum evaporation to give 15.9 g of a whitish oily residue. The latter is chromatographed on a high performance preparative chromatograph (2 operations) on silica, in petroleum ether containing ether (80/20 v/v) to give 13.5 g (70%) of compound no. 4 in the form of an analytically pure, clear oil. By bubbling gaseous HCl into the etheral solution of said compound, its white solid hydrochloride is precipitated and which, recovered by suction filtering and vacuum drying, melts at 205° to 207° C. (analytically pure).

Percentage analysis of the product of empirical formula $C_{18}H_{28}NOCl$:

| | Found | Calculated |
|---|---|---|
| C | 70.02 | 69.79 |
| H | 9.24 | 9.05 |
| N | 4.55 | 4.52 |

EXAMPLE 9

Preparation of the r-(hydroxymethyl-3-piperidino)-1-c-methyl-4 (thienyl-2)-1 cyclohexane of formula:

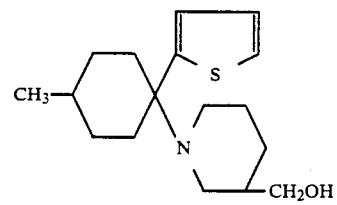

(compound no. 5)

The Grignard reagent resulting from the action of 31 g (0.19M) of 2-bromothiophene on 4.8 g (0.20M) of magnesium in the form of turnings is prepared in 200 ml of anhydrous ether. To it is slowly added 9 g (0.04M) of synthon IV dissolved in 200 ml of anhydrous ether. Stirring takes place for 12 hours on the reflux condenser, the complex is decomposed by a cold, saturated solution of NH4Cl and then, after settling, the liquids are extracted with ether (3×150 ml). The combined ethereal phases are extracted by an aqueous 20% HCl solution (2×150 ml). The acid liquids are neutralized by NH4OH, extracted with ether (3×150 ml) and then the collected ethers, following drying (Na2SO4) are evaporated in vacuo to give 9 g of a yellowish oily residue. The latter is chromatographed on a high performance preparative chromatograph on silica, in hexane containing ether (95/5 v/v) to give 7.5 g (67%) of compound no. 5 in the form of an analytically pure, clear oil. By bubbling gaseous HCl into the ethereal solution of said compound, its solid white hydrochloride is precipitated and which, recovered by suction filtering and vacuum drying, melts at 186° to 187° C. (analytically pure).

Percentage analysis of the product of empirical formula $C_{17}H_{29}NOSCl$:

| | Found | Calculated |
|---|---|---|
| C | 61.62 | 61.91 |
| H | 8.56 | 8.50 |
| N | 4.34 | 4.25 |

EXAMPLE 10

Preparation of the acetate of ((hydroxymethyl-3-piperidino)-1)-1 phenyl-1 cyclohexane of formula:

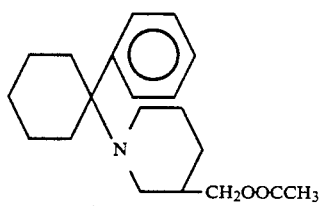

(compound no. 6)

3 g (0.01M) of compound no. 4 are placed in a mixture of 3 g (0.03M) of acetic anhydride and 2 g (0.03M) of anhydrous pyridine. The solution is stirred at 25° C. for 24 h and then poured into a large volume of water and ice, which is violently stirred for 30 min. The solution is extracted with ether (3×50 ml), the dried ethers (Na₂SO₄) are evaporated in vacuo to leave a whitish oily residue of 3.3 g. The latter is chromatographed on alumina in pure petroleum ether to give 2.7 g (78%) of compound no. 6 in the form of an analytically pure, clear oil. By bubbling gaseous HCl into the ethereal solution of said compound, its solid white hydrochloride is precipitated and which, recovered by suction filtering and vacuum drying, decomposes at 180° C. (analytically pure).

Percentage analysis of the product of empirical formula $C_{20}H_{30}NO_2Cl$:

|   | Found | Calculated |
|---|-------|------------|
| C | 68.25 | 68.28 |
| H | 8.84  | 8.54  |
| N | 3.66  | 3.98  |

EXAMPLE 11

Preparation of the ((fluoro-3 phenyl)-1)-r-((hydroxymethyl-3 piperidino)-1)-1-c-methyl-4 cyclohexane of formula:

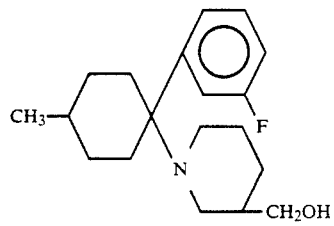

(compound no. 7)

The Grignard reagent resulting from the action of 7.5 g (0.04M) of 1-bromo-3-fluorobenzene on 1 g (0.04M) of magnesium in the form of turnings is prepared in 50 ml of anhydrous ether. To it is slowly added 2 g (0.08M) of synthon IV dissolved in 50 ml of anhydrous ether. Stirring takes place for 12 h on the reflux condenser and the complex is decomposed by a cold, saturated NH₄Cl solution and then, after settling, the liquids are extracted with ether (3×50 ml). The combined ethereal phases are extracted by an aqueous 20% HCl solution (2×50 ml). The acid liquids are neutralized by NH₄OH, extracted with ether (3×50 ml) and then, after drying (Na₂SO₄) the collected ethers are evaporated in vacuo to give 1.7 g of a brownish oily residue. The latter is chromatographed on a high performance preparative chromatograph on silica, in pentane containing ether (80/20 v/v) in order to give 1.2 g (46%) of compound no. 7 in the form of analytically pure, clear oil. By bubbling gaseous HCl into the ethereal solution of said compound, its solid white hydrochloride is precipitated and, after recovery by suction filtering and vacuum drying, it de-composes at 218° C. (analytically pure).

Percentage analysis of the product of empirical formula $C_{19}H_{29}NOFCl$:

|   | Found | Calculated |
|---|-------|------------|
| C | 66.68 | 66.76 |
| H | 8.39  | 8.49  |

-continued

|   | Found | Calculated |
|---|-------|------------|
| N | 3.88  | 4.10 |

EXAMPLE 12

Preparation of the [(chloromethyl-3 piperidino)-1]-1 (thienyl-2)-1 cyclohexane of formula:

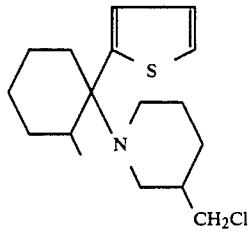

(compound no. 8)

To 2.5 g (0.009M) of compound no. 3 and 1 ml of methylene chloride is very slowly added (with evacuation or trapping for acid gases) and accompanied by stirring, 1 g of thienyl chloride dissolved in 1 ml of methylene chloride. This is followed by heating for 6 hours at 60° C. and evaporation of the solvent in vacuo. The residue obtained is diluted in 10 ml of water and carefully neutralized with 20% NH₄OH. The liquids are extracted with ether (3×20 ml), the collected ethers are dried (Na₂SO₄) and evaporated in vacuo, which gives 2.4 g of a brownish oily residue. The latter is purified by flash chromatography on silica, in petroleum ether, in order to give 2.1 g (78%) of compound no. 8 in the form of an analytically pure, clear oil. By bubbling gaseous HCl in the ethereal solution of said compound, its solid white hydrochloride is precipitated and, after recovery by suction filtering and vacuum drying, it melts at 150° to 151° C. (analytically pure).

Percentage analysis of the product of empirical formula $C_{16}H_{25}NSCl_2$:

|   | Found | Calculated |
|---|-------|------------|
| C | 57.18 | 57.49 |
| H | 7.58  | 7.49  |
| N | 4.28  | 4.19  |

EXAMPLE 13

Preparation of the c-methyl-2-r-(piperidino-1)-1 (thienyl-2)-1 cyclohexane of formula:

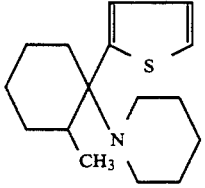

(compound no. 9)

A) The Grignard reagent resulting from the action of 8.25 g (0.05M) of 2-bromothiophene on 2 g (0.08M) of magnesium in the form of turnings is prepared in 75 ml of anhydrous ether. To it is added 5.6 g (0.05M) of 2-methyl-cyclohexanone dissolved in 75 ml of anhydrous ether. Stirring takes place for 3 h on the reflux condenser, the complex is decomposed by a cold, saturated NH₄Cl solution and then, after settling, the liquids are extracted with ether (3×50 ml). After drying (Na₂SO₄) the ethers are evaporated in vacuo to give 8.7 g (88.8%) of a mixture of epimeric alcohols (Ir). The alcohols are not otherwise purified as the following reaction takes place by carbocation.

B) At −5° C. preparation takes place of a suspension containing 6.5 g (0.1M) of sodium azide, 82 g (0.5M) of trichloroacetic acid and 100 ml of chloroform and vigorously stirred. To it is slowly added and dissolved in 70 ml of chloroform and at the same temperature, 8.7 g (0.045M) of the previously obtained alcohols. Stirring and the temperature are maintained for 3 h (or until the alcohols disappear) which is followed by cold neutralization with NH₄OH, settling, extraction of the aqueous phase or chloroform (2×50 ml) and washing of the collected organic phases to a neutral pH value. After drying (Na₂SO₄) and vacuum evaporation, an oily residue is recovered, which weights 8.85 g and which essentially contains two unsaturated derivatives (highly minority) and two epimeric azides (IR) which, bearing in mind their relative instability, are not otherwise purified.

C) The mixture of the two azides previously obtained from 8.85 g is dissolved in 100 ml of isopropanol and heated to 65° C. Portionwise addition takes place of Raney nickel (whilst maintaining the temperature) until the giving off of gas stops. This is followed by heating to 70° C. for 15 minutes, cooling to ambient temperature, filtering on celite, washing the latter with 100 ml of isopropanol, the addition of 200 ml of 20% HCl to the alcoholic phases and vacuum evaporation in order to eliminate the isopropanol. The cooled, residual aqueous phase is neutralized by NH₄OH. This is followed by the extraction with ether (3×50 ml, drying (Na₂CO₃) and evaporation of the solvent in vacuo to obtain 4.6 g of an oily residue, which essentially contains two epimeric primary amines (IR, GC/MS).

D) The preceding amines (4.6 g) are dissolved in 100 ml of acetonitrile containing 5.2 g of 1,5-dibromopentane and 13 g of K₂CO₃. The highly stirred mixture is refluxed for 72 h and then cooled to ambient temperature. After filtering, addition takes place of 150 ml of 20% HCl, extraction with ether (2×50 ml) and the acid liquids, neutralized by NH₄OH are in turn extracted with ether (3×50 ml). After drying, (Na₂CO₃), the ethers are evaporated in vacuo to give 3.7 g of an oily residue essentially containing two isomeric tertiary amines (IR, GC/MS).

The mixture obtained is chromatographed on a high performance preparative chromatograph on silica in hexane, containing ether (95/5 v/v) to give a first clear oil fraction, which slowly crystallizes (40° to 41° C.) and which is analytically pure of 1.7 g of t-methyl-2-r-(piperidino-1)-1 (thienyl-2)-1 cyclohexane; a second fraction of white crystals of 1.4 g (80° to 81° C.) which is analytically pure of compound no. 9 or c-methyl-2-r-(piperidino-1)-1 (thienyl-2)-1 cyclohexane and two other fractions representing 400 mg in all and constituted by primary amines which have not reacted and whose mixture is recyclable during a subsequent synthesis. By bubbling gaseous HCl into the ethereal solution of the crystallized bases, their solid white hydrochlorides are precipitated and, after recovery by suction filtering and vacuum drying, they melt respectively at 152° to 153° C. and 220° to 221° C. for compound no. 9, HCl. The yield of compound no. 9 base from the starting ketone is 10.5%. Therefore the two stereoisomeric structures are easily differentiated by NMR of ¹³C (CDCl₃) from the hydrochlorides (anancomeric conformations). In compound no. 9, HCl, methyl, carbons C₂, C₄ and C₆ are more shielded than in the isomer with a lower melting point, as a result of the axial position of the methyl (instead of the equatorial position in the other isomer).

Percentage analysis of the product of empirical formula C₁₆H₂₆NSCl:

|   | Found | Calculated |
|---|-------|------------|
| C | 64.23 | 64.11 |
| H | 8.69  | 8.68 |
| N | 4.59  | 4.67 |

EXAMPLE 14

Preparation of the t-methyl-4-r-(piperidino-1)-1 (thienyl-2-1 cyclohexane of formula:

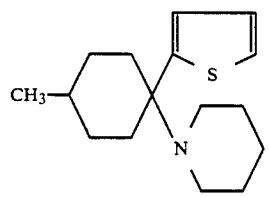

(compound no. 10)

A) The Grignard reagent resulting from the action of 49.5 g (0.3M) of 2-bromothiophene on 8.75 g (0.35M) of magnesium in the form of turnings is prepared in 300 ml of anhydrous ether. To it is added 22.4 g (0.2M) of 4-methyl-cyclohexanone dissolved in 300 ml of anhydrous ether. Stirring takes place for 3 h on the reflux condenser, the complex is decomposed by a cold, saturated NH₄Cl solution and then, after settling, the liquids are extracted with ether (3×200 ml). The dried ethers (Na₂SO₄) are evaporated in vacuo to give a yellowish solid which, after crystallization in petroleum ether, gives 31.4 g (80%) of a white solid in the form of a mixture of epimeric alcohols (IR). As the following reaction takes place by carbocation, the alcohols are not otherwise purified.

B) At −5° C. a suspension is prepared containing 4.9 g (0.075M) of sodium azide, 61 g (0.37M) of trichloroacetic acid and 35 ml of chloroform and vigorously stirred. To it is slowly added, dissolved in 50 ml of chloroform and at the same temperature, 6 g (0.031M) of the previously obtained alcohols. The stirring and temperature are maintained for 3 h (or until the alcohols disappear), followed by cold neutralization with NH₄OH, settling, extraction of the aqueous phase with chloroform (2×50 ml) and the washing of the collected organic phases up to a neutral pH value. After drying (Na₂SO₄) and evaporation in vacuo, an oily residue weighing 5.75 g is recovered and this essentially contains an unsaturated derivative (highly minority) and two epimeric azides (Ir) which, bearing in mind their relative instability, are not otherwise purified.

C) The mixture of the two previously obtained azides (5.75 g) is dissolved in 100 ml of isopropanol and heated to 65° C. Raney nickel is added portionwise (while maintaining the temperature) until the giving off of gas stops. This is followed by heating to 70° C. for 15 min, cooling to ambient temperature, filtering on celite, washing the latter with 100 ml of isopropanol, adding 200 ml of 20% HCl to the alcoholic phases and evaporation in vacuo in order to eliminate the isopropanol, the cooled, residual aqueous phase being neutralized by NH4OH. This is followed by extraction with ether (3×50 ml), drying (Na2CO3) and evaporation of the solvent in vacuo in order to finally isolate 3.8 g of an oily residue, which essentially contains two epimeric primary amines (IR, GC/MS).

D) The preceding amine mixture (3.8 g) is dissolved in 50 ml of acetonitrile containing 4.3 g of 1,5-dibromopentane and 11 g of K2CO3. The vigorously stirred mixture is refluxed for 72 h and is then cooled to ambient temperature. After filtering, 100 ml of 20% HCl are added, followed by extraction with ether (2×50 ml) and the acid liquids, neutralized by NH4OH, are in turn extracted with ether (3×50 ml). After drying (Na2CO3), these ethers undergo vacuum evaporation to give 3.2 g of an oily residue essentially containing two isomeric tertiary amines (IR, GC/MS). The mixture obtained is chromatographed on alumina. The petroleum ether elutes a first analytically pure, clear oil fraction of 1.1 g of c-methyl-4-r-(piperidino-1)-1(thienyl-2)-1 cyclohexane, a second fraction of white crystals representing 1.5 g (68° to 69° C.) in analytically pure form of compound no. 10 or t-methyl-2-r-(piperidino-1)-1(thienyl-2)-1 cyclohexane and two other fractions representing 300 mg in all and constituted by primary amines, which have not reacted and whose mixture is recyclable during a subsequent synthesis. By bubbling gaseous HCl into the ethereal solution of the crystallized bases, their white solid hydrochlorides are precipitated and, after recovery by suction filtering and vacuum drying, they respectively melt at 206° to 208° C. and 162° to 163° C. for compound no. 10 HCl. The yield of compound no. 10 base from the starting ketone is 18.5%. The two stereoisomeric structures are easily differentiated by NMR of $^{13}C$ (CDCl3) from the hydrochlorides (enantiomeric conformations). In compound no. 10, HCl, methyl, the carbons $C_2$, $C_6$ and $C_4$ are more unshielded than in the isomer eluted at the top, due to the equatorial position of the methyl (instead of the axial position in the other isomer).

Percentage analysis of the product of empirical formula $C_6H_{26}NSCl$:

|   | Found | Calculated |
|---|-------|------------|
| C | 63.88 | 64.11 |
| H | 8.64  | 8.68 |
| N | 4.64  | 4.68 |

EXAMPLE 15

Preparation of the t-hydroxy-2 phenyl-1-r-(piperidino-1)-1 cyclohexane of formula:

(compound no. 11)

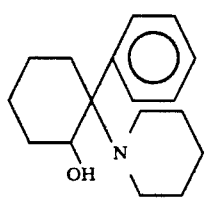

A) The Grignard reagent resulting from the action of 48.9 g (0.3M) of bromobenzene on 8.75 g (0.35M) of magnesium in the form of turnings is prepared in 300 ml of anhydrous ether. To it is added 19.6 g (0.2M) of cyclohexanone dissolved in 300 ml of anhydrous ether. Stirring takes place for 3 h on the reflux condenser and the complex is decomposed by a cold, saturated NH4Cl solution and then, after settling, the liquids are extracted with ether (3×200 ml). The ethers are dried (Na2SO4) and evaporated in vacuo to give a yellowish solid which, after two crystallizations in petroleum ether, give 25 g of white 1-phenyl-cyclohexanol melting at 60° to 61° C. (IR).

B) To 17.6 g (0.1M) of the previously melted alcohol are added, accompanied by stirring, 20 ml of a mixture of sulphuric acid and acetic acid (20/80 v/v). After 30 sec, the mixture is poured on to 100 ml of water and ice and then extracted with ether (3×20 ml). The ethers are washed with water and dried (Na2SO3), followed by vacuum evaporation and the remaining liquid is distilled under reduced pressure (0.5 mmHg) to give a fraction (86° to 88° C.) of 11.8 g (75%) of pure 1-phenyl-cyclohexene (IR).

C) 20 g (0.125M) of the preceding 1-phenyl-cyclohexene are placed in 200 ml of anhydrous ether and to it are slowly added, accompanied by stirring, 26.6 g (0.15M) of m-chloroperbenzoic acid dissolved in 200 ml of anhydrous ether. Stirring takes place for 12 h at 25° C., followed by the addition of a 10% NaOH solution in a quantity adequate to precisely neutralize the reacted acid. This is followed by settling, washing of the grouped ethers to a neutral pH, drying the same (Na2SO4), followed by vacuum evaporation thereof to obtain 20.8 g of crude epoxide. The latter is chromatographed on neutral alumina in petroleum ether containing ether (95/5 v/v), in order to obtain 17.8 g of an analytically pure transparent oil (81%).

D) 10.5 g (0.06M) of epoxide and 30.8 g (0.36M) of piperidine are dissolved in 47 g of methanol. After refluxing for 6 days accompanied by stirring, it is poured into a mixture of water and ice, extracted with ether (3×100 ml), the latter are extracted by 20% HCl (2×100 ml) and the acid phase is neutralized by NH4OH. The liquids are extracted with ether (3×100 ml), the dried ethers (Na2SO4) are evaporated hot in vacuo to give 13.4 g of yellowish solid. After several crystallizations in hexane, the latter gives 2.4 g (15.4%) of compound no. 11 in the form of an analytically pure white solid melting at 133° to 134° C. By bubbling gaseous HCl into the ethereal solution of said compound, its solid white hydrochloride is precipitated and, after recovery by suction filtering and vacuum drying, it melts at 203° to 205° C.

Percentage analysis of the product of the empirical formula $C_{17}H_{25}NO$:

|   | Found | Calulated |
|---|-------|-----------|
| C | 78.61 | 78.77 |
| H | 9.80  | 9.65 |
| N | 5.22  | 5.40 |

The attached table 1 gives the results of the NMR spectra of $^{13}C$ of compounds 1 to 11. The spectra were recorded in CDCl3 at 20.147 MHz in ppm based on tetramethyl silane (TMS), the compounds either being in the form of the base, or in the form of the hydrochloride (designated by an asterisk).

EXAMPLE 16

Simple Rotary Bar Test

In this example, the properties of compounds 1 to 5 and 8 to 11 are tested on Swiss mice.

Different doses of the compounds to be tested are administered subcutaneously to the mice and the latter are then placed in batches of 10 on a rotary bar, being separated from one another by separating disks. This bar is made from scraped wood, has a diameter of 3 cm and is moved horizontally with a uniform circular movement about its axis at a speed of 10 rpm.

Determination takes place of the $ED_{50}$, which is the dose at which 50% of the animals drop, the dose being expressed in mg/kg.

The results are given in table 2. On the basis of these results, it can be seen that all the compounds according to the invention are active, because the $ED_{50}$ is below 25 mg/kg, with the exception of compound no. 8, which has a low activity compared with the other compounds.

EXAMPLE 17

Affinity of the Compounds for the Sites of PCP and TCP

This test serves to determine the affinity of certain compounds of examples 5 to 15 by competition experiments on the homogenates of the brains of rats. The radioactive ligands used are $(^3H)PCP$ at an activity of 45 Ci/mmole and $(^3H)TCP$ at an activity of 62 Ci/mmole.

A fixed concentration of the tritiated ligand (1 nmole) is incubated in the presence of increasing concentrations of the compound to be tested and the homogenate (1 mg of protein per ml) in a 50 mM Hepes-tris buffer medium at a pH of 7.7 at 25° C. At equilibrium, the concentration of the tested compound preventing the fixing of 50% of the tritiated ligand (IC50) reflects the affinity of the latter for the considered receptor.

The results obtained are given in table 2. On the basis of these results, it can be seen that the compounds of the invention are very active, because the concentrations necessary for preventing the fixing of 50% of the tritiated ligand are very low.

EXAMPLE 18

Inhibition Test of the Synaptosomal Striatal sample of $(^3H)DA$

This test is carried out according to the method used by Vignon and Lazdunski operating in the following way. Wistar rats weighing 200 to 250 g are killed by cervical dislocation. Their brains are rapidly removed and the striae dissected on ice. The striae are then homogenized with a Teflon glass Potter homogenizer in 50 volumes of tris HCl 10 mM buffer containing 0.32M of sucrose at pH 7.4 and they are centrifuged at 1000 g for 10 min. The supernatants are further centrifuged at 10000 g for 20 min. The resulting deposits $P_2$ containing the crude synaptosomes are used without supplementary purification.

The synaptosomes are balanced with the compound to be tested for 30 min at 30° C. in the Ringer medium (mM: 140 NaCl, 5 KCl, 2.6 $CaCl_2$, 1.3 $MgSO_4$, 10 tris-HCl, pH=7.4)+200 μM of pargyline. This is followed by the addition of $(^3H)DA$ labelled dopamine at a final concentration of 5 nM for 5 min at 30° C. and sampling is interrupted by filtration of the incubate (150 μl) on GF/B filters. The non-specific sample is measured at 4° C. in parallel incubations and is deducted from the total sample at 30° C. The IC50 is the compound concentration preventing 50% of the specific capture compared with the control in the absence of an inhibitor.

The results obtained are given in table 2.

EXAMPLE 19

Competition Test with 3H-QNB for the Cerebral Cholinergic Muscarinic Receptor In these tests, a fixed concentration of tritiated ligand ($^3$H-QNB) is incubated in the presence of variable concentrations of compounds to be tested and a rat brain homogenate with approximately 1 mg of protein/ml.

The concentration of compound preventing the fixing of 50% of the tritiated ligand (IC50) is a measure of the affinity of said compound for the cerebral cholinergic muscarinic receptor. The fixing of the tritiated ligands to the homogenate is determined by the method of rapid filtering on Whatman GF/B glass filters.

The results obtained are given in table 2. On the basis of these results, it can be seen that the compounds tested generally had very little affinity for the muscarinic cholinergic receptor.

EXAMPLE 20

Competition Test with $H^3DHM$ for the Receptor of the Opiates.

In this test, a fixed concentration of $^3$H-DHM labelled morphine was incubated in the presence of variable concentrations of the tested compound and a rat brain homogenate. The concentration of the compound preventing the fixing of 50% of $^3$H-DHM (IC50) is a measure of the affinity of the compound for the receptor of the opiates. The result obtained is given in table 2. The latter also gives the results obtained with PCP and TCP, as well as the ratios $H^3DA/^3H$-TCP, $^3HQNB/^3H$-TCP and $^3HDHM/^3HTCP$ obtained with the different tested compounds.

On the basis of this table, it can be seen that the selectivity of the compounds according to the invention for the PCP site compared with the DA, QNB and DHM sites is much greater than in the case of PCP and TCP.

It can also be seen that the $^3HDA/^3H$-TCP ratio is higher than 100 with the compounds used in the invention, whereas it is respectively only 2.5 and 25.39 for PCP and TCP.

EXAMPLE 21

This example illustrates the effect of the arylcyclohexylamines according to the invention on in vitro cultures of rat brain cells as a neuroprotector against acute attacks caused by the presence of glutamate.

Cortical and hippocampal neuron cultures were prepared from the fetuses of rats aged from 17 to 18 days. The hemispheres or hippocampi are dissected and immersed in a buffer containing EDTA (Verséne) for 10 min. The tissues are then mechanically dissociated in a saline PUCK solution free from calcium and magnesium and centrifuged at 70 g for 10 min. The centrifuging deposit is resuspended in a culture medium constituted by 60% of the minimum essential Eagle medium (MEM), 25% of a saline Hank solution, 5% of human serum, 5% of calf foetus serum, 5% of embryo extract and which are complemented with 6% glucose. The cells are introduced at a density of $10^6$ cells per ml into 24 Wells previously coated with polylysine D. The cultures are allowed to grow for 3 weeks, ⅔ of the culture medium being renewed every 3 days. The test is carried out in the following way. Glutamate dissolved in 10 μl of MEM is added to the medium in order to obtain a final glutamate concentration of $5 \cdot 10^{-4}$M. After exposure for 5 min, the medium is changed. For studying the antagonist derivatives of the glutamate, to the culture medium is added the compound to be test in 10 μl of MEM in order to obtain a final concentration of compound of 200, 20 or $0.2 \cdot 10^{-6}$M. Five minutes later, glutamate is added to the medium and then the medium is replenished after exposure for 5 minutes. The protected and unprotected cultures are then examined and photographed at intervals between 30 min and 24 h.

After culturing for 3 weeks, the cortical neurons appear as a mixture of bright cells ranging from a small to a medium size and where the nuclei and nucleoli are sometimes bright. They grow at the top of a monolayer of flat cells, the majority of which are astrocytes immunoreactive to the fibrillar acid protein. In the cultures of hippocampal neurons and cortical neurons, the acute exposure to the glutamate has the effect of a rapid swelling associated with an increased granularity of the bodies of the cells. Such a phenomenon is also observed in control cells following rapid washing. After 3 h exposure to the glutamate, the cells retract and there is a progressive necrosis of the neurons and 24 h afterwards there is a maximum neuron loss. In most cases, the only surviving neurons are found after 24 h in the cortical cultures, whereas the hippocampal neurons have been completely damaged.

However, on adding to the cultures 20 μmole of compound no. 2 according to the invention, the cultures are only very slightly damaged. With 2 μmole of compound no. 2, there is only a limited protection and with 0.2 μmole no protection, as is indicated by the results of table 3 obtained 24 h after 5 min exposure to the glutamate. This protective effect is observed against the acute swelling, which is less intense and the necrosis, which is completely blocked. After 24 h, whilst the necrosis is at a maximum in the glutamate-treated cells, the cultures of hippocampal and cortical cells appear healthy in the same way as the control cells.

Thus, the compound according to the invention has an effective protective effect on hippocampal and cortical neurons with respect to the damage due to in vitro glutamate. These results confirm the protective effect of non-competitive antagonists of NMDA.

With regards to the mechanism used for this protection, it is assumed that a massive influx of $Ca^{2+}$ produced by the activation of the NMDA receptors is involved in the death of the neurons.

The compounds used in the invention reduce or block the $Ca^{2+}$ and its lethal consequences. This protective effect is probably reinforced by the presence of the glutamate released in an endogenous or exogenous manner and the compounds are consequently very effective for the treatment of acute attacks due to the presence of the glutamate.

EXAMPLE 22

This example illustrates the effect of the arylcyclohexylamines according to the invention on in vitro cultures of cortical and hippocampal neurons taken from the fetuses of rats aged 17 to 18 days.

Firstly cortical/hippocampal neuron cultures were prepared as in example 21 by introducing cells at a density of $10^6$ cells/ml into the wells and then allowing the cultures to grow for 12 to 25 days, whilst renewing ⅓ of the culture medium every 3 days. The cultures were then treated with the compound to be tested, so as to obtain a final compound concentration of 20 μmole/liter. Following this treatment, an evaluation took place of the neuronal survival either by direct examination of the living cells in phase contrast, or after fixing and immunocytochemical labelling by antibodies directed against neuronal enolase.

With this treatment, there is a survival of a large number of neurons below the two months used for culturing, whereas generally with such a culture type, the life of the neurons scarcely exceeds 30 days.

The best time for carrying out this treatment is at the start of the third culture week, which corresponds to the period in which the neurons become sensitive to the acute toxicity of the exciting amino acids naturally present in the culture medium.

EXAMPLE 23

This example also illustrates the effect of the arylcyclohexylamines according to the invention on the in vitro neuron culture survival. As in example 21, cortical and hippocampal neuron cultures are prepared. At the start of the third culturing week, the cells are treated with a single dose of the compound to be tested and culturing is continued for two months. At the end of this period, the cells which were fixed and dyed to reveal the specific enolase of the neurons are subject to counts in order to determine the quantity of cells per surface unit.

The results obtained are given in FIG. 1, which is a histogram indicating the number of cells/mm² which survived after 2 months culturing.

The results are given for the control, i.e. for untreated cultures, cultures treated with 2.5 and 20 μmole/l of TCP, cultures treated by compound no. 9 at concentrations of 2.5 and 5 μmole/l and cultures treated by compound MK801 at concentrations of 2.5 and 5 μmole/l. Compound MK801, which is known to have a neuroprotection activity, is (+)-methyl-5-dihydro-10,11(5H)dibenzo(A,D) cycloheptenimine-5,10 of formula:

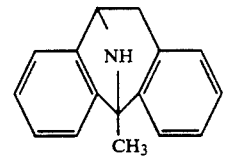

From FIG. 1 it can be seen that the control cultures, after surviving for 2 months, on average contain 50 neurons/mm². The treated cultures, no matter what the compound and dose used, contain more than 500 neurons/mm².

This experiment was also carried out with doses higher than those given in FIG. 1, but significantly different results were not obtained.

It is pointed out that compound 9 at a dose of 5 μmole/liter gives a comparable result to that of TCP at 20 μmole/l and that of MK801 at 5 μmole/l.

It can be concluded from this experiment that the life of neurons cultured in vitro can be considerably extended by a single treatment with molecules, which are non-competitive antagonists of the MMDA receptor. In addition, compound 9 according to the invention has an effectiveness equal to that of the reference compound MK801. Therefore the compounds according to the invention are of great interest in combating neuronal aging.

EXAMPLE 24

This example illustrates the effect of arylcyclohexylamines on cerebral aging. No matter what the cause of the cerebral aging (vascular or degenerative), it leads to a neuronal loss at the cerebral cortex, the hippocampas and to a lesser extent the cerebellum. This cellular loss can be quantified by simple histological methods and evaluated on a larger scale by means of semi-automatic image analysis methods.

In this example 6 mice aged 23 months by intraperitonealy injecting 3 of them with 5 mg/kg of TCP in the physiological solute at the 23rd, 24th and 25th months and 3 other mice were intraperitonealy injected with the physiological solute only. At the 26th month, all the mice were sacrificed by intracardial perfusion of a 5% glutaraldehyde solution, the brains were cut up with the vibratone and the sections dyed by the NISSL method.

The results obtained are given in FIGS. 2 to 5, which are sections of the brain and the cerebellum of the treated mice and the untreated control mice.

Figure 2:
Figure 3:
Figure 4:
Figure 5:

FIG. 3 shows at the cerebellum a rarefication of the Purkinjé cells (in the zone indicated by the arrows), whereas in FIG. 2 said rarefication is much less significant in the zone indicated by the arrows. In the same way, in FIG. 5 there is a rarefaction of the pyramidal cells $Ca_3$ of Ammon's horn at the hippocampas (in the zone indicated by the arrow), which is much less marked in the zone indicated by the arrow of FIG. 4, which corresponds to the treated mice.

This experiment was repeated using compound no. 9 in place of TCP and equivalent results were obtained. Thus, TCP and the arylcyclohexylamines according to the invention are effective in combating cerebral aging.

The arylcyclohexylamines according to the invention have a low toxicity, so that the subcutaneous $LD_{50}$ in the rat exceeds 60 mg/kg for compounds 3 and 4.

TABLE 1

NMR SPECTRA OF $^{13}$C

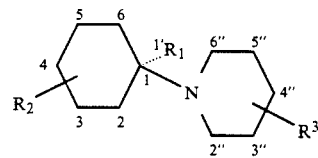

| | | | | COMPOUNDS | | | | | | | |
|---|---|---|---|---|---|---|---|---|---|---|---|
| N* | 1* | 2* | 3* | 4 | 4 | 6 | 7* | 8* | 9 | 10* | 11* |
| 1 | 70.6 | 69.2 | 69.8 | 60.5 | 58.8 | 60.5 | 71.3 | 69.9 | 63.5 | 68.8 | 73.4 |
| 2 | <u>30.5</u> | <u>32.7</u> | <u>33.3</u> | <u>33.5</u> | <u>35.6</u> | <u>33.5</u> | 25.4 | 33.2 | 30.5 | 32.8 | 75.8 |
| 3 | 22.4 | <u>22.6</u> | 22.90 | 22.1 | <u>29.7</u> | 22.1 | 28.3 | 23.0 | 28.9 | 31.0 | 33.1 |
| 4 | 24.3 | 23.7 | 23.9 | 26.2 | 32.2 | 26.2 | 25.7 | 23.9 | 19.8 | 30.3 | 24.7 |
| 5 | 22.4 | <u>22.6</u> | 22.9 | 22.1 | <u>29.6</u> | 22.1 | 28.3 | 23.0 | 22.8 | 31.0 | 22.6 |
| 6 | <u>30.5</u> | <u>32.6</u> | <u>33.0</u> | <u>33.3</u> | <u>35.4</u> | <u>33.0</u> | 25.4 | 33.2 | 26.9 | 32.8 | 33.1 |
| 1' | 130.0 | 135.6 | 135.9 | 140.3 | 147.6 | 140.3 | 132.7 | 136.0 | 137.3 | 136.3 | 133.7 |
| 2" | 46.5 | <u>43.7</u> | 49.7 | 48.7 | 49.0 | 48.7 | 50.1 | <u>48.9</u> | 46.0 | 47.0 | 53.2 |
| 3" | <u>30.3</u> | 119.4 | 36.6 | 36.1 | 38.9 | 36.1 | 36.8 | 34.5 | 27.0 | 22.6 | <u>23.5</u> |
| 4" | 29.3 | 125.5 | 25.3 | 25.1 | 25.3 | 25.1 | 25.7 | 26.1 | 25.2 | 22.1 | 22.6 |
| 5" | <u>30.3</u> | 23.2 | 22.2 | 27.4 | 27.6 | 27.4 | 22.2 | 21.7 | 27.0 | 22.6 | <u>24.1</u> |
| 6" | 46.5 | <u>42.9</u> | 46.8 | 46.1 | 46.0 | 46.1 | 47.0 | <u>46.4</u> | 46.0 | 47.0 | 50.2 |
| R2 | — | — | — | — | 22.1 | — | 17.7 | — | 13.7 | 21.0 | — |
| R3 | 20.4 | — | 64.2 | 66.3 | 67.0 | 67.0 | 64.2 | <u>47.5</u> | — | — | — |
| CO | — | — | — | — | — | 170.6 | — | — | — | — | — |

*compound in hydrochloride form
— the underlined values can be transposed.

TABLE 2

| Compound No. | $ED_{50}$ (mg/kg) | $^3$H-PCP $IC_{50}$ ($10^{-6}$ M) | $^3$HTCP $IC_{50}$ ($10^{-6}$ M) | $^3$HDA $IC_{50}$ ($10^{-6}$ M) | $^3$HQNB $IC_{50}$ ($10^{-6}$ M) | $^3$HDHM $IC_{50}$ ($10^{-6}$ M) | $^3$HDA/ $^3$H-TCP | $^3$HQNB/ $^3$HTCP | $^3$HDHM/ $^3$HTCP |
|---|---|---|---|---|---|---|---|---|---|
| 1 | 20 | 0.4 | — | 5.0 | — | | 125 | — | — |
| 2 | 4.0 | 0.017 | 0.026 | 4.7 | 25 | | | 961 | |
| 3 | 0.68 | 0.7 | | | 90 | | | 128 | |
| 4 | 1.8 | 1.0 | | | 100 | | | 100 | |
| 5 | 8 | 0.38 | | | 110 | | | 289 | |
| 6 | | 1.1 | | | 140 | | | 127 | |
| 7 | | 4.5 | | | 760 | | | 168 | |
| 8 | 150 | 0.56 | | | 870 | | | 1553 | |
| 9 | 3.5 | 0.04 | 0.019 | 7.9 | 12 | 5.0 | 415 | 631 | 263 |
| 10 | 19.0 | 0.14 | 0.034 | 3.6 | 29.3 | | 105 | 862 | |
| 11 | 17 | 1.17 | | | 125 | | | 106.8 | |
| PCP | 4 | 0.25 | 0.20 | 0.5 | 30 | 26 | 2.5 | 150 | 130 |
| TCP | 2.3 | 0.026 | 0.063 | 1.6 | 21 | 11 | 25.39 | 333 | 74.6 |

TABLE 3

| Compound No. 2 | 200 μM | 20 μM | 2 μM | 0.2 μM |
| --- | --- | --- | --- | --- |
| Treatment of cortical cells | − | − | + | ++ |
| Treatment of hippocampal cells | − | − | + | ++ |

++: severe damage
+: partial protection
−: no damage.

What is claimed is:

1. A method of treating a human being to prevent cerebral attacks which occur during acute ailments or diseases and to protect the brain against neuronal loss or to extend neuronal life in the cerebral cortex, the hippocampus and the cerebellum by administering to a human being in need thereof an effective amount of a neuroprotective medicament including as its active ingredient an arylcyclohexylamine in accordance with the formulas:

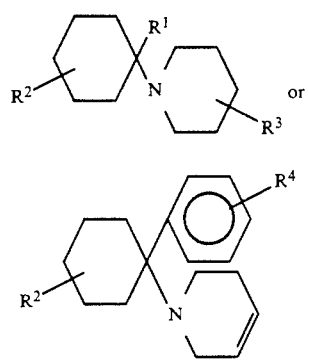

in which:
R$^1$ represents

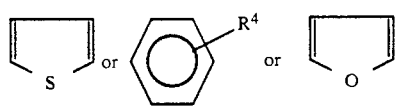

with R$^4$ being a hydrogen atom, a fluorine atom, an iodine atom or a methyl radical, R$^2$ a hydrogen atom, the OH radical or the CH$_3$ radical and R$^3$ a hydrogen atom or the radical CH$_2$R$^5$ with R$^5$ representing H, OH, Cl, Br or CH$_3$COO, provided that R$^2$ and R$^3$ are not both a hydrogen atom, or an addition salt to a pharmaceutically acceptable acid of said arylcyclohexylamine.

2. A method according to claim 1, characterized in that the arylcyclohexylamine is in accordance with the formula:

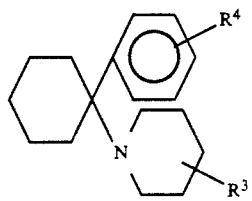

in which R$^3$ stands for the methyl radical or the radical CH$_2$R$^5$ with R$^5$ representing OH or CH$_3$COO and R$^4$ stands for a hydrogen atom.

3. A method according to claim 1, characterized in that the arylcyclohexylamine is in accordance with the formula:

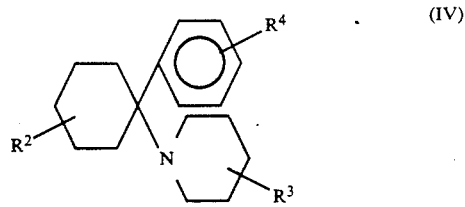

in which R$^2$ is the methyl radical, R$^3$ the radical CH$_2$R$^5$ with R$^5$ representing OH and R$^4$ is a fluorine atom.

4. A method according to claim 1, characterized in that the arylcyclohexylamine is in accordance with formula:

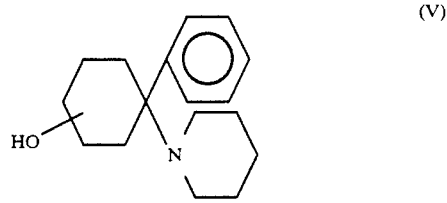

5. A method according to claim 1, characterized in that the arylcyclohexylamine is in accordance with formula:

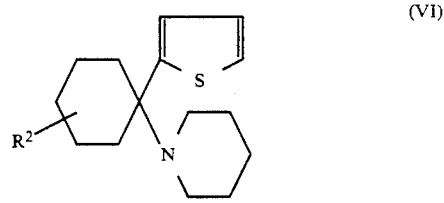

in which R$^2$ is the methyl radical.

6. A method according to claim 1, characterized in that the arylcyclohexylamine is in accordance with the formula:

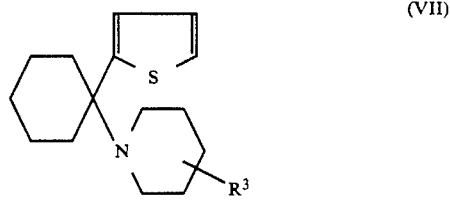

in which R$^3$ is the CH$_2$R$^5$ radical with R$^5$ representing OH or Cl.

7. A method according to claim 1, characterized in that the arylcyclohexylamine is in accordance with the formula:

8. A method according to claim 1, characterized in that the arylcyclohexylamine is in accordance with the formula:

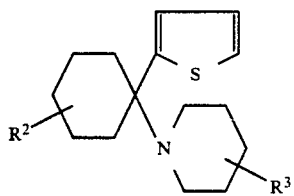
(VIII)

in which $R^2$ is the methyl radical and $R^3$ the radical CH₂OH.

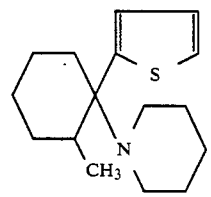

in which CH₃ is in the cis position with respect to the piperidine.

9. A method according to any one of the claims 1, 3, 4, 5 and 7, characterized in that $R^2$ is in the ortho position.

10. A method of treating a human being to prevent cerebral attacks which occur during acute ailments or diseases and to protect the brain against neuronal loss or to extend neuronal life in the cerebral cortex, the hippocampus and the cerebellum by administering to a human being in need thereof an effective amount of a neuroprotective medicament including as its active ingredient the compound TCP of formula:

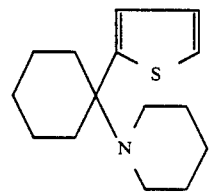

* * * * *